United States Patent [19]

Hofeditz et al.

[11] Patent Number: 4,552,138

[45] Date of Patent: Nov. 12, 1985

[54] DRESSING MATERIAL BASED ON A HYDROGEL, AND A PROCESS FOR ITS PRODUCTION

[75] Inventors: Wolfgang Hofeditz; Joachim Hornig; Werner Karmann, all of Hamburg, Fed. Rep. of Germany

[73] Assignee: Beiersdorf Aktiengesellschaft, Hamburg, Fed. Rep. of Germany

[21] Appl. No.: 502,362

[22] Filed: Jun. 8, 1983

[30] Foreign Application Priority Data

Jun. 30, 1982 [DE] Fed. Rep. of Germany ....... 3224382

[51] Int. Cl.$^4$ ............................................. A61L 15/01
[52] U.S. Cl. .................... 128/156; 424/26; 424/28
[58] Field of Search ............... 128/156; 424/DIG. 13, 424/28, 31, 32, 78, 81, 33; 524/386, 389, 803; 523/111; 525/330.6, 383; 521/141; 428/26, 27, 28; 427/391, 393.5

[56] References Cited

U.S. PATENT DOCUMENTS

| | | | |
|---|---|---|---|
| 2,609,347 | 9/1952 | Wilson | 521/141 |
| 2,647,100 | 7/1953 | Salditt | 128/156 |
| 2,664,366 | 12/1953 | Wilson | 521/141 |
| 2,693,438 | 11/1954 | Ward | 424/28 |
| 3,287,222 | 11/1966 | Larde et al. | 128/156 |
| 3,339,546 | 9/1967 | Chen | 128/156 |
| 3,858,379 | 1/1975 | Graves | 523/111 |
| 4,098,728 | 7/1978 | Rosenblatt | 521/141 |
| 4,342,745 | 8/1982 | Mirkovitch | 424/78 |

FOREIGN PATENT DOCUMENTS

| | | |
|---|---|---|
| 0095892 | 12/1983 | European Pat. Off. |
| 2422308 | 9/1975 | Fed. Rep. of Germany |
| 2618613 | 11/1977 | Fed. Rep. of Germany |

*Primary Examiner*—Veronica P. Hoke
*Attorney, Agent, or Firm*—Sprung, Horn, Kramer & Woods

[57] ABSTRACT

Dressing material of at least one layer of a polymeric, hydrophilic gel and, where relevant, one or more layers of a carrier material as an intermediate and/or covering layer, wherein the gel consists of 40–50% by weight of a polyvinyl alcohol which is crosslinked and acetalized with formaldehyde and is water-insoluble to the extent of at least 90%, 15–30% by weight of water, 15–45% by weight of one or more polyhydric alcohols with 2–6 C atoms and, where relevant, small amounts of additives and/or auxiliaries.

17 Claims, No Drawings

DRESSING MATERIAL BASED ON A HYDROGEL, AND A PROCESS FOR ITS PRODUCTION

The invention relates to a new dressing material based on a transparent, water-containing, flexible polyvinyl alcohol gel, which is preferably in the form of a film and, where relevant, can be combined with one or more layers of another carrier material as an intermediate and/or covering layer, and to the process for the production of the dressing material.

Hydrogels and hydrogel-containing dressing materials of the most diverse gel-forming agents, for example of vinyl-crosslinked polyethylene oxides, polyurethaneureas, polysiloxanes, mixtures of gelable polysaccharides and/or proteins and hydrophilic polymers or graft polymers of hydrolyzed starch and polyacrylonitrile, are already known from the patent literature. The disadvantage of these gels is in most cases their low mechanical strength in the swollen state, so that they crumble and disintegrate under mechanical load. Although there is a great need for such dressing agents, especially for the treatment of burn wounds and similar wounds of large area, they have therefore hitherto found no use at all or only very limited use in practice.

It is furthermore known that water-soluble polyvinyl alcohol films can be hardened and thereby rendered water-insoluble by treatment with aldehydes, such as formaldehyde, glyoxal and glutarodialdehyde. Foams based on formaldehyde-crosslinked polyvinyl alcohol are also known. Because of their good physiological tolerance, they are used in the treatment of wounds. However, these films and foams are rigid and unflexible in the dry state.

The object of the invention was therefore to develop a dressing material consisting of at least one layer of an elastic, transparent, water-swellable but water-insoluble physiologically very well tolerated gel film which has a high mechanical stability and high flexibility both in the dry and in the swollen state, optionally additionally with other supporting or absorbent materials as an intermediate or covering layer.

This object is achieved by a dressing material which consists of at least one layer of a polymeric, hydrophilic gel and, if desired, one or more layers of a carrier material, as an intermediate and/or covering layer, wherein the gel consists of 40–50% by weight of a polyvinyl alcohol which is crosslinked and acetalized with formaldehyde and is water-insoluble to the extent of at least 90%, 15–30% by weight of water, 15–45% by weight of a polyhydric alcohol with 2–6 C atoms and, where relevant, small amounts of additives and/or auxiliaries.

A polyvinyl alcohol which has an average molecular weight (viscosity average) of 15,000 to 110,000, preferred 65000–85000, a degree of hydrolysis of 85–90%, preferably 88%, and a viscosity of 3–40 cP, preferably about 18 cP, in 4% strength aqueous solution at 20° C. is used as the starting material for the preparation of the polyvinyl alcohol which is substantially crosslinked and acetalized with formaldehyde and is virtually no longer soluble, ie. is at most still soluble to the extent of 5–10%, in cold and hot water.

Particularly suitable polyhydric alcohols, which act as plasticizers for the film, are those with 2–6 C atoms and two or 3 hydroxyl-groups (particularly alkanediols or alkane-triols), and of these especially ethylene glycol, diglycol, tri-glycol, glycerol, propanediol, butanediol, hexanediol and hexanetriol. The gel can contain the alcohols, individually or as mixtures, in amounts of 15–45% by weight, preferably 20–30% by weight, depending on the desired flexibility of the gel film. 1,2-Propanediol has proved to be particularly advantageous.

Additives and/or auxiliaries which the gel can contain in small amounts are to be understood as meaning, in particular, medicinal active compounds, such as antibiotics, for example gentamycin, or polyvinylpyrrolidone-iodine, physiologically acceptable dyestuffs, pigments, fragrances, fillers in the form of fibers or powders, or preservatives.

The soft and flexible gel according to the invention is prepared by dissolving the still uncrosslinked polyvinyl alcohol (PVAL) in water, acidifying this solution with an acid, preferably hydrochloric acid, adding an aqueous formaldehyde solution in an amount such that, when the reaction has ended, no further free aldehyde can be detected, and leaving the solution to react, ie. precrosslink, at 50°–80° C., preferably 60°–70° C., for several hours, whereupon the reaction product (prepolymer) is obtained as a gelatinous mass. After the hydrochloric acid has been removed, advantageously by neutralizaton with sodium hydroxide solution and subsequent washing several times with water, a plastic-soft, water-containing mass is obtained, into which the additives mentioned and the plasticizers can easily be incorporated by intermixing.

The pre-crosslinked gel is spread out or poured out in the desired layer thickness, as a rule about 0.5 to a few mm thick, on an auxiliary carrier, for example a siliconized Kraft paper and is then dried to a residual water content of 15–30% by weight, preferably about 25% by weight, and at the same time thereby further crosslinked, by subsequent heat treatment (for about one hour at 80°–100° C.).

The gel films obtained in this manner are flexible and elastomeric as a result of the plasticizer and water content; they are tear-resistant and virtually water-insoluble as a result of the high crosslinking, and thereby still have a water absorption capacity of about 600–800%, which is particularly important for their usefulness as dressing agents. The films are also transparent, so that the wound can be observed through them, but are impermeable to bacteria. Moisture can diffuse through them in vapor form.

The gel films according to the invention can be placed on the wound as such, since they have sufficient secretion-absorbency and tear strength, but they are preferably processed to a laminated product with one or more other carrier materials and are used in this form. Particularly suitable materials for this are fine woven fabrics or non-woven fabrics, for example based on polyamide, polyurethane or polyester, or open-pore foams, which are embedded in the gel during preparation, or highly absorbent materials in the form of foams, woven fabrics, knitted fabrics of non-woven fabrics which are based on plastics or natural substances and are laminated onto the gel film. Protective films, which may be impermeable to water vapor, can also be anchored onto the gel as a covering layer.

These further carrier layers are advantageously laminated into or onto the pre-crosslinked gel layer, to which they adhere well, and are bonded still more firmly with this gel during subsequent further crosslinking.

The ready-to-use dressing materials can then be finished in the desired manner and preferably sealed in bags which are impermeable to water vapor and sterilized, for example by γ-radiation.

The elastic and water-containing polyvinyl alcohol films according to the invention are particularly suitable for wounds which have hitherto still been difficult to tend, such as large-area burn and abrasion wounds, or for covering areas where skin has been removed. They act like a synthetic skin or membrane which provides an optimum medium by keeping the wound base moist but not wet and producing a temperature favorable to healing by slow removal of excess moisture by diffusion. At the same time, they protect the wound from external contamination, including bacterial contamination. As experiments have shown, normal granulation tissue with capillary branches and aligned collagen fibers is formed under the cover. If the gel is also doped with active compounds, for example 0.25–0.5% by weight of gentamycin or 0.1–0.15% by weight of polyvinylpyrrolidone-iodine, it thereby additionally has a bactericidal action and hence promotes healing.

The examples which follow are intended to illustrate the production of the dressing materials according to the invention in more detail.

EXAMPLE 1

416.5 g of aqueous polyvinyl alcohol solution (12% strength, degree of hydrolysis about 88%, viscosity of a 4% strength aqueous solution at 20° C.: 18 cp) and 96.5 g of hydrochloric acid (32% strength) are initially introduced into a flask with a ground-glass joint and a stirrer and are heated to 70° C., and 14 g of aqueous formaldehyde solution (35% strength) are added dropwise.

The mixture is left to react at this temperature for three hours and is neutralized with sodium hydroxide solution, and the mass which has precipitated as a gel is then washed thoroughly with hot water. The pre-crosslinked polyvinyl alcohol is separated off from the excess washing water and 20% by weight of glycerol is incorporated. In this stage, additional dyestuffs, active compounds and other additives can also be intermixed, if desired.

The homogeneous soft mass is then spread onto release paper (siliconized Kraft paper) in the desired coating thickness (about 0.5–2 mm) and dried, and further crosslinked, in a hot air cabinet at 80°–90° C. for 1 hour.

The resulting film has a residual moisture of 10–15%, a water absorption capacity of about 600–800% and a water evaporation rate of 35–40 mg/cm$^2$/24 hours in the swollen state.

It is transparent, resilient and mechanically very stable both in the dry state and in the swollen state.

EXAMPLES 2–4

The procedure followed is as described in Example 1, but, instead of glycerol as the plasticizer, 25% of propane-1,2-diol or, in addition to the propanediol, 6% of aluminum powder or 2% of polyvinylpyrrolidone-iodine, are incorporated into the prepolymer precipitated.

These gel films are also pliable, resilient and, depending on the plasticizer content, more or less soft.

EXAMPLES 5–6

The layer of a pre-crosslinked, still moist mass according to Example 2, ie. with a plasticizer content of 25% of propane-1,2-diol, which has been spread out is laminated with a non-woven fabric or an open-pore foam of polyethylene, polypropylene, polyurethane or polyester and the laminate is then subjected to the drying and further crosslinking process.

In each case a laminated product which has a high moisture absorption capacity and has the properties of the combined materials is formed.

EXAMPLE 7

A thin polyamide woven fabric is coated and impregnated with the pre-crosslinked mass according to Example 2, so that it is included in the gel film after drying and further crosslinking and serves to strengthen the film internally.

What is claimed is:

1. A wound dressing material of at least one layer of a polymeric, hydrophilic gel and, where relevant, one or more layers of a carrier material as an intermediate and/or covering layer, wherein the gel comprises 40–50% by weight of a polyvinyl alcohol which is crosslinked and acetalized with formaldehyde and is water-insoluble to the extent of at least 90%, 15–30% by weight of water, and 15–45% by weight of one or more polyhydric alcohols with 2–6 carbon atoms.

2. A dressing material as claimed in claim 1, wherein the polyvinyl alcohol has a degree of hydrolysis of 85–90%, and a viscosity of 3–40 cp, in 4% strength aqueous solution before its reaction with formaldehyde.

3. A dressing material as claimed in claim 1, wherein the gel contains a polyhydric alcohol selected from the group consisting of ethylene glycol, di-glycol, tri-glycol, glycerol, propanediol, butanediol, hexanediol, hexanetriol, and mixtures thereof.

4. A dressing material as claimed in claim 3, wherein the gel contains 20–30% by weight of propane-1,2-diol.

5. A dressing material as claimed in claim 1, wherein the gel layer is combined with intermediate and/or covering layers of woven fabrics, knitted fabrics, non-woven fabrics or foams on a synthetic or natural basis to give a laminated product.

6. A process for the production of a flexible gel layer as claimed in claim 1, which comprises dissolving 40–50% by weight, in each case based on the end product, of polyvinyl alcohol in water, reacting the solution with formaldehyde at elevated temperature, incorporating 15–45% by weight of one or more polyhydric alcohols with 2–6 carbon atoms and, where relevant, small amounts of other additives or auxiliaries into the reaction product which has been precipitated and washed, spreading the resultant soft mass out in the form of a sheet or web in the desired thickness and then subjecting the mass to further heat treatment, for about one hour at about 80°–100° C., for purpose of drying to a residual water content of 15–30% by weight and at the same time conducting further crosslinking.

7. A process as claimed in claim 6, wherein the gel layer is provided with intermediate and/or covering layers by embedding into the layer of pre-crosslinked gel spread out, or laminating onto this layer, a web of woven fabric, non-woven fabric, film or open-pore foam based on a natural substance or a plastic, and then subjecting the laminated product to heat treatment for drying and further crosslinking.

8. A dressing material as claimed in claim 2, wherein the said degree of hydrolysis is 88%.

9. A dressing material as claimed in claim 2, wherein the said viscosity is 18 cp.

10. A dressing material according to claim 1, wherein the alcohol contains two or three hydroxyl groups.

11. A dressing material as claimed in claim 1, wherein the alcohol has an average molecular weight of 15,000 to 110,000.

12. A dressing material as claimed in claim 1, wherein the alcohol has an average molecular weight of 65,000 to 85,000.

13. A dressing material as claimed in claim 1, wherein additives and/or auxiliaries are present which are selected from the group consisting of medicinal active compounds, physiologically acceptable dyestuffs, physiologically acceptable pigments, physiologically acceptable fragrances and physiologically acceptable fillers.

14. A dressing material according to claim 12, wherein the active compound is selected from the group consisting of antibiotics and polyvinylpyrrolidone-iodine.

15. A dressing material according to claim 14, wherein the antibiotic is gentamycin and is contained in an amount of 0.25–0.5% by weight.

16. A dressing material according to claim 14, wherein said polyvinylpyrrolidone-iodine is contained in an amount of 0.1–0.15% by weight.

17. In a method of treating a wound on a patient including placing a dressing on the wound of the patient, the improvement which comprises said dressing being the dressing of claim 1.

* * * * *